United States Patent [19]

Toshima

[11] Patent Number: 4,937,406

[45] Date of Patent: Jun. 26, 1990

[54] INSULATOR-TYPE GAS CIRCUIT INTERRUPTER

[75] Inventor: Norichika Toshima, Amagasaki, Japan

[73] Assignee: Mitsubishi Denki Kabushiki Kaisha, Japan

[21] Appl. No.: 284,711

[22] Filed: Dec. 14, 1988

[30] Foreign Application Priority Data

Feb. 23, 1988 [JP] Japan .................................. 63-40044

[51] Int. Cl.[5] .............................................. A01H 33/54

[52] U.S. Cl. ............................ 200/148 R; 200/148 A

[58] Field of Search ......................... 200/148 R, 148 A

[56] References Cited

U.S. PATENT DOCUMENTS 4,365,126 12/1982 Oshima et al. .................. 200/148 R

FOREIGN PATENT DOCUMENTS 47-22468 11/1972 Japan .

60-84044 6/1985 Japan .

*Primary Examiner*—Robert S. Macon

*Attorney, Agent, or Firm*—Leydig, Voit & Mayer

[57] ABSTRACT

An insulator-type gas circuit interrupter which comprises a movable contact and a stationary contact for closing and separating a main circuit and an insulator tube in which an arc-extinguishing chamber of a frustoconical configuration is defined. The movable contact is disposed in the frustoconical arc-extinguishing chamber at its smaller inner diameter side, and the stationary contact is disposed in the frustoconical arc-extinguishing chamber at its larger inner diameter side. An electrically insulating gas is sealed inside of the frustoconical arc-extinguishing chamber.

1 Claim, 3 Drawing Sheets

INSULATOR-TYPE GAS CIRCUIT INTERRUPTER

BACKGROUND OF THE INVENTION

This invention relates to an insulator-type gas circuit interrupter which utilizes the inside of an insulator tube as an arc extinguishing chamber.

A general structure of a typical insulator-type gas circuit interrupter is shown in FIG. 1, and a cross section of a conventional insulator-type gas circuit interrupter disclosed in Japanese Utility Model Laid-Open No. 47-22468 for example is shown in FIG. 2. In both of the figures, the same reference numerals designate identical or corresponding components.

In FIG. 1, the typical insulator-type gas circuit interrupter comprises an insulator tube 1 having disposed therein a movable contact and a stationary contact (not shown) for opening and closing a main circuit, a support insulator 2 for supporting the insulator tube 1, and a housing 3 having disposed therein a drive mechanism (not shown because it is well known) for driving the movable contact and for fixedly supporting the support insulator 2. The insulator tube 1 is cylindrical in order that its interior can be utilized as an arc extinguishing chamber, and the top and the bottom of the cylindrical section are sealed by flanges 4 and 5. Each of the flanges 4 and 5 is provided with a terminal 6 and 7, respectively for connection to the main circuit. A drive mechanism (not shown) for driving the movable contact (not shown) is disposed within the housing 3, so that the typical structure is one where the stationary contact is disposed at the upper portion of the insulator tube 1 and the movable contact is disposed at the lower portion of the insulator tube 1.

A conventional insulator-type gas circuit interrupter as disclosed in Japanese Utility Model Laid-Open No. 47-22468 will next be described in conjunction with FIG. 2, which illustrates the interrupted state.

An insulator tube 1, which is a tapered ceramic tube for example, defines an arc extinguishing chamber 1*a* by closing an upper and a lower opening 1*b* and 1*c* with flanges 4 and 5. An electrically insulating gas 18 such as $SF_6$ gas is filled within the arc extinguishing chamber 1*a*. A stationary contact support post 8 extends from the flange 4 downwardly along the central axis of the insulator tube 1. At the tip of the stationary contact support post 8, an arcing stationary contact 10 is disposed along the axis of the insulating tube 1 and a cluster of current carrying stationary contacts 9 is disposed to face the arcing stationary contact 10. An exhaust port 8*a* is formed between the arcing stationary contact 10 and the current carrying stationary contact 9 in order to discharge a flow of an insulating gas generated upon the arc extinguishing operation.

On the other hand, the flange 5 is provided thereon around the central axis of the insulator tube 1 with sliding contacts 13. A piston rod 16 is provided to oppose the stationary contact support post 8 so as to be reciprocally movable by a known drive mechanism. At the tip of the piston rod 16, an arcing movable contact 15 and a puffer cylinder 12 are provided. At the tip of the puffer cylinder 12, a current carrying movable contact 11 which is a contact material of a different metal welded to the tip is provided. At the tip of the current carrying movable contact 11, an insulating nozzle 14 is provided. Therefore, the piston rod 16, the arcing movable contact 15, the puffer cylinder 12, the current carrying movable contact 11 and the insulating nozzle 14 are physically integral with each other, so that they are reciprocatingly moved by the previously described known drive mechanism, and they are electrically connected to the flange 5 except for the insulating nozzle 14 by the puffer cylinder 12 and the piston rod 16 slide-contacting with the sliding contacts 13.

In the puffer cylinder 12, an exhaust port 12*a* is formed for discharging the insulating gas within the puffer cylinder 12. Also, terminals 6 and 7 are disposed on the flanges 4 and 5 for the connection to the main circuit.

In the conventional circuit interrupter, since the movable contact side must be made structurally large-sized due to a larger number of components and the provision of the puffer cylinder 12 as compared to the stationary contact side, the insulator tube 1 is arranged to have a smaller inner diameter at the stationary contact side than at the movable contact side.

The operation of the conventional circuit interrupter will now be described.

When an electric current is to be interrupted with a conventional insulator-type gas circuit interrupter of the above construction, the piston rod 16 is driven in the direction shown by an arrow X by a well-known drive mechanism from a position (closed position; not shown) in which the current carrying stationary contact 9 engages the current carrying movable contact 11, and in which the arcing stationary contact 10 engages the arcing movable contact 15. Since the current carrying stationary contact 9 and the current carrying movable contact 11 separate from each other before the arcing stationary contact 9 and the arcing movable contact 15 separate from each other, an electric arc 19 generates across the arcing stationary contact 10 and the arcing movable contact 15. As the puffer cylinder 12 moves in the arrow-X direction, the insulating gas within the puffer cylinder 12 is discharged along an arrow 18*a* through an exhaust port 12*a* to be blasted at the arc 19 generated across the arcing stationary contact 10 and the arcing movable contact 15. The insulating gas blasted at the arc 19 then flows along an arrow 18*b* and is discharged from an exhaust port 8*a* in the stationary contact support post 8 in the direction of arrows 18*c* and 18*d*. The thermal energy of the arc 19 is absorbed by the insulating gas and is expanded to be extinguished. The above arc-extinguishing principle and the arc extinguishing mechanism are well known as a puffer-type gas circuit interrupter.

The insulating gas which has been blasted at an electric arc and heated by the absorption of the thermal energy of the arc contains contact material molten upon the arc generation, so that the insulating gas is degraded in insulating property and may even have an electrical conductivity. On the other hand, in the conventional insulator-type gas circuit interrupter, since the inner diameter of the insulator tube 1 at the stationary contact side is small, the distance between the tube 1 and the stationary contact support post 8 is small, providing a problem that there is a possibility that the the stationary contact support post 8 and the insulator tube 1 are short-circuited by the high temperature, electrically conductive gas discharged from the exhaust port 8*a* in the stationary contact support post 8.

Also, while the heat generated during the current conduction generally tends to stay in the upper portion of the arc extinguishing chamber, the conventional insulator-type gas circuit interrupter does not have sufficient heat dissipating surface area due to the reduced diameter upper portion of the insulator tube 1, whereby the carrying current is disadvantageously limited.

SUMMARY OF THE INVENTION

The present invention has been made in order to solve the above-discussed problem and has as its object the provision of an insulator-type gas circuit interrupter in which short-circuiting relative to the insulator tube by a heated insulating gas is prevented and in which the heat dissipating characteristics are superior.

The insulator-type gas circuit interrupter of the present invention comprises a movable contact and a stationary contact for closing and separating a main circuit and an insulator tube in which an arc extinguishing chamber of a frustoconical configuration is defined. The movable contact is disposed in the frustoconical arc extinguishing chamber at its smaller inner diameter side, and the stationary contact is disposed in the frustoconical arc extinguishing chamber at its larger inner diameter side. An electrically insulating gas is sealed inside of the frustoconical arc extinguishing chamber.

The insulator tube has therein the frustoconical arc-extinguishing chamber, and the movable contact is disposed at the smaller-diameter side of the arc-extinguishing chamber and the stationary contact is disposed at the larger-diameter side of the chamber. Within the interior of the arc-extinguishing chamber, an electrically insulation gas such as $SF_6$ gas is filled. As is well known, the insulator-type gas circuit interrupter generally has the stationary contact mounted at the upper portion and the movable contact and the drive mechanism therefor mounted at the lower portion.

The movable contact and the stationary contact, which are disposed within the interior of the frustoconical arc-extinguishing chamber within the insulator tube, close and open the main circuit by being thrown-in and interrupted. Upon the separation of the movable contact and the stationary contact, an electric arc is generated across these elements. The arc is elongated as the movable contact moves and at the same time its thermal energy is absorbed by the insulating gas such as $SF_6$ gas filled within the arc-extinguishing gas to be cooled and extinguished.

The insulating gas which has absorbed the thermal energy of the arc contains molten contact material within the arc and sometimes becomes degraded in insulation and electrically conductive. Such gas may be present in the space between the stationary contact and the inner wall of the insulator tube. However, since the inner diameter of the arc-extinguishing chamber within the insulator tube is made larger at the stationary contact side, the distance between the stationary contact and the inner surface of the insulator tube can be made sufficiently large, whereby short-circuiting due to the non-insulating gas which has absorbed the thermal energy of the remaining arc does not occur. At the same time, a ssufficiently large heat dissipating surface area is provided toward the exterior of the insulator tube, so that the heat that built up during the ordinary current conduction state can effectively be dissipated.

BRIEF DESCRIPTION OF THE DRAWINGS

The present invention will become more readily apparent from the following detailed description of the preferred embodiment of the present invention taken in conjunction with the accompanying drawings, in which.

DESCRIPTION OF THE PREFERRED EMBODIMENT

The present invention will now be described in terms of one embodiment of the insulator-type gas circuit interrupter.

Figure 1:
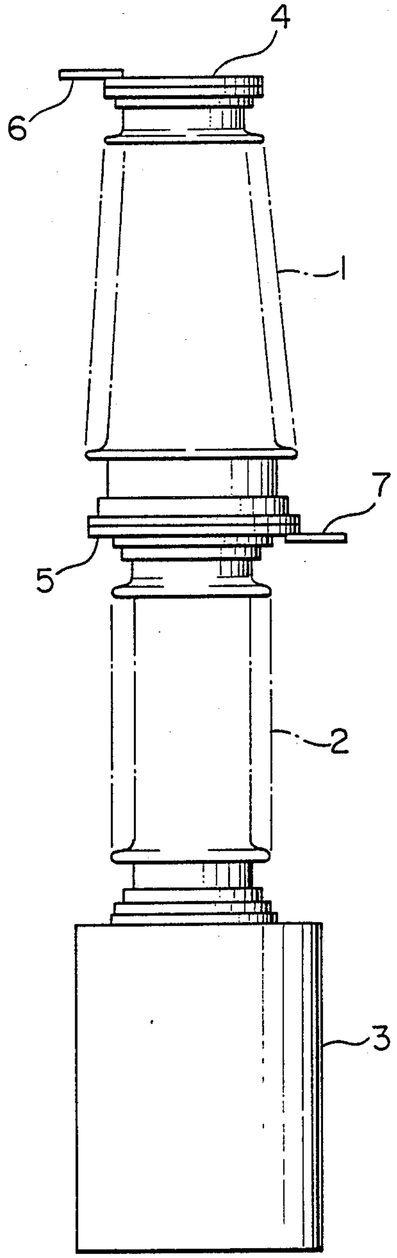
FIG. 1 PRIOR ART
FIG. 1 is a view showing the typical appearance of a conventional insulator-type gas circuit interrupter.
Figure 2:
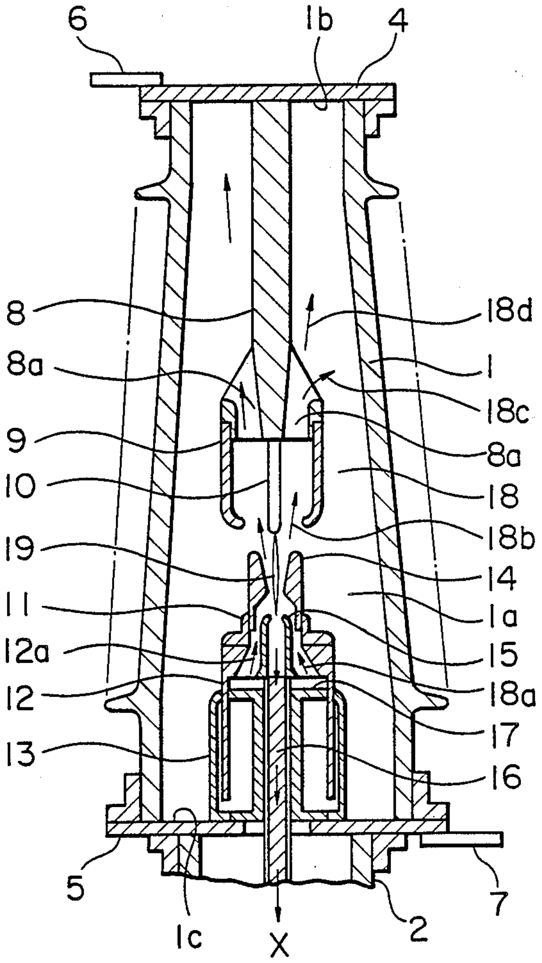
FIG. 2 PRIOR ART
FIG. 2 is a sectional view showing the structure of the conventional insulator-type gas circuit interrupter.
Figure 3:
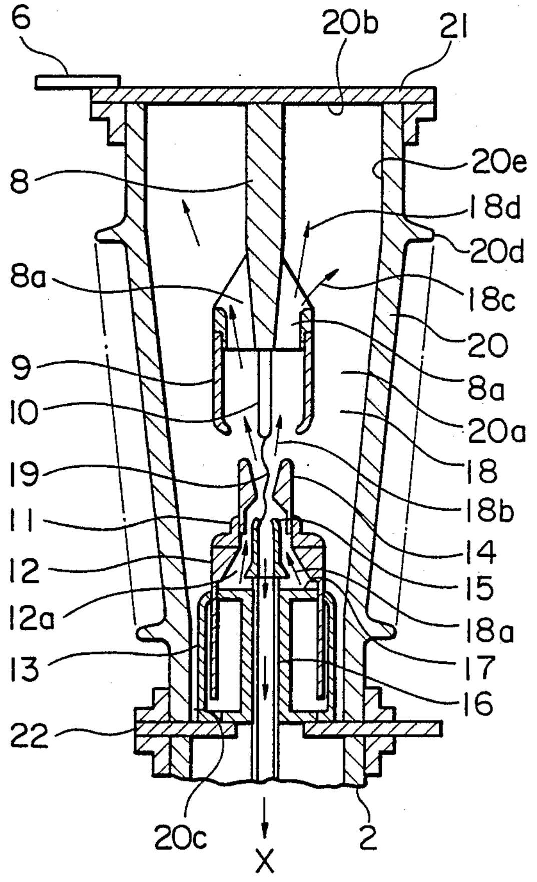
FIG. 3 is a sectional view showing the structure of one embodiment of the insulator-type gas circuit interrupter of the present invention.

FIG. 3 is a sectional view of the insulator tube of the insulator-type gas circuit interrupter of the present invention. Throughout the drawings, the same reference numerals designate identical or corresponding components.

An insulator tube 20 is a tapered hollow insulator tube made of ceramic or the like, upper and lower openings 20*b* and 20*c* are closed by flanges 21 and 22, respectively, to define an arc-extinguishing chamber 20*a*. An electrically insulating gas 18 such as $SF_6$ gas is filled within the arc-extinguishing chamber 20*a*. The insulator tube 20 is oriented with the larger inner diameter upward and the smaller inner diameter downward and has heat dissipating sheds 20*d* disposed at equal intervals at the outer periphery for heat dissipation or the like. The heat dissipation sheds 20*d* are bevelled at their upper surface and flat at their lower surface as seen from the figures.

A stationary contact support post 8 extends from the flange 21 downwardly along the central axis of the insulator tube 20. At the tip of the stationary contact support post 8, an arcing stationary contact 10 is disposed along the axis of the insulating tube 20 and a cluster of current carrying stationary contacts 9 annularly surrounding the arcing stationary contact 10 is disposed. An exhaust port 8*a* is formed between the arcing stationary contact 10 and the current carrying stationary contact 9 in order to discharge a flow of an insulating gas generated upon the arc extinguishing operation.

On the other hand, the flange 22 is provided thereon around the central axis of the insulator tube 20 with sliding contacts 13. A piston rod 16 is provided to oppose the stationary contact support post 8 so as to be reciprocally movable by a known drive mechanism (not shown). At the tip of the piston rod 16, an arcing movable contact 15 and a puffer cylinder 12 are provided. At the tip of the puffer cylinder 12, a current carrying movable contact 11 and an insulating nozzle 14 are provided. Therefore, the piston rod 16, the arcing movable contact 15, the puffer cylinder 12, the current carrying movable contact 11 and the insulating nozzle 14 are physically integral with each other, so that they are reciprocatingly moved by the previously described known drive mechanism, and they are electrically connected to the flange 22 except for the insulating nozzle 14 by the puffer cylinder 12 and the piston rod 15 slide-contacting with the sliding contacts 13. In the puffer cylinder 12, an exhaust port 12*a* is formed for discharging the insulating gas within the puffer cylinder 12. Also, the terminal 6 is disposed on the flange 21 for an electrical connection to the main circuit. The flange 22 has the conventional terminal 7.

The operation of this embodiment will now be described.

When an electric current is to be interrupted with an insulator-type gas circuit interrupter of the present invention having the above construction, the piston rod 16 is driven into the direction shown by arrow X by a well-known drive mechanism from the position (closed position; not shown) in which the current carrying stationary contact 9 engages the current carrying movable contact 11, and in which the arcing stationary contact 10 engages the arcing movable contact 15. Since the current carrying stationary contact 9 and the current carrying movable contact 11 separate from each other before the arcing stationary contact 10 and the arcing movable contact 15 separate from each other, an electric arc 19 generates across the arcing stationary contact 10 and the arcing movable contact 15. As the puffer cylinder 12 moves in the direction of arrow X, the insulating gas within the puffer cylinder 12 is discharged along arrow **18*a* through an exhaust port 12*a* to be blasted at the arc 19 generated across the arcing stationary contact 10 and the arcing movable contact 15. The insulating gas blasted at the arc 19 then flows along arrow 18*b*, and is discharged from an exhaust port 8*a* in the stationary contact support post 8 in the direction of arrows 18*c* and 18*d*. The thermal energy of the arc 19** is absorbed by the insulating gas and is expanded to be extinguished. The above arc-extinguishing principle and the arc extinguishing mechanism are well known as a puffer-type gas circuit interrupter.

Upon generation of the arc, the arcing stationary contact 10 and the arcing movable contact 15 melt and the molten contact material is contained in the insulating gas as plasma. The insulating gas discharged from the exhaust port **8*a* impinges against the inner wall 20*e* of the insulator tube 20, causing the molten contact material to attach on the inner wall. The insulator tube 20 is degraded in its insulation where the contact material attaches and some times become electrically conductive in an extreme case. However, as apparent also from FIG. 3, the insulator tube 20 of the insulator-type gas circuit interrupter is constructed to have a larger inner diameter at the stationary contact side or the upper portion and a smaller inner diameter at the movable contact side or the lower portion, so that the distance between each of the stationary contact support post 8, the current carrying stationary contact 9, the arcing stationary contact 10 and the like and the portion of the inner wall 20*e* of the insulator tube 20** to which the molten contact material attaches increases, thereby preventing insulation breakdown even when the conductive gas (or non-insulating gas) remains.

While the above description has been made in terms of a single-break insulator-type gas circuit interrupter, the present invention can be equally applied to a multi-break insulator-type gas circuit interrupter.

As has been described, the inner diameter of the insulator tube is larger at the stationary contact side than at the movable contact side, so that no short-circuiting occurs across the inner wall of the insulator tube and the stationary contact. Also, the heat dissipating surface area becomes large, preventing heat builds up in the upper portion of the insulator tube during the ordinary current carrying condition.

What is claimed is:

1. An insulator-type gas circuit interrupter comprising a movable contact and a stationary contact for closing and separating a main circuit; and an insulator tube in which an arc extinguishing chamber of a frustoconical configuration is defined, said movable contact is disposed in said frustoconical arc extinguishing chamber at its smaller inner diameter side, said stationary contact is disposed in said frustoconical arc extinguishing chamber at its larger inner diameter side, and in which an electrically insulating gas is sealed inside of said frustoconical arc extinguishing chamber.

* * * * *